United States Patent [19]
Biber et al.

[11] Patent Number: 5,825,535
[45] Date of Patent: Oct. 20, 1998

[54] PANCRATIC MAGNIFICATION SYSTEM

[75] Inventors: Klaus Biber, Aalen; Fritz Strahle, Heubach, both of Germany

[73] Assignee: Carl Zeiss Stiftung, Heidenheim, Germany

[21] Appl. No.: 555,962

[22] Filed: Nov. 13, 1995

[30] Foreign Application Priority Data

Nov. 12, 1994 [DE] Germany .......................... 44 40 530.8

[51] Int. Cl.⁶ .......................... G02B 21/12; G02B 21/22; G02B 15/14; G02B 21/00
[52] U.S. Cl. .......................... 359/380; 359/377; 359/389; 359/686; 359/823; 359/696; 359/699
[58] Field of Search .......................... 359/380, 372–379, 359/389, 363, 686, 823, 694, 699, 696

[56] References Cited

U.S. PATENT DOCUMENTS

| | | | |
|---|---|---|---|
| 4,155,622 | 5/1979 | Klein | 359/379 |
| 4,175,826 | 11/1979 | Blaha et al. | 350/36 |
| 4,235,509 | 11/1980 | Takabayashi et al. | 359/380 |
| 4,354,203 | 10/1982 | Koyama | 352/140 |
| 5,140,458 | 8/1992 | Takagi et al. | 359/380 |
| 5,223,981 | 6/1993 | Kaneda | 359/696 |
| 5,227,914 | 7/1993 | Hanzawa et al. | 359/380 |
| 5,394,267 | 2/1995 | Hanzawa | 359/380 |

FOREIGN PATENT DOCUMENTS

| | | | |
|---|---|---|---|
| 4123279 | 6/1992 | Germany . | |
| 4212924 | 1/1993 | Germany . | |
| 4336715 | 4/1994 | Germany . | |
| 404159508A | 2/1995 | Japan | 359/376 |

Primary Examiner—Jon W. Henry

[57] ABSTRACT

A pancratic magnification system for at least two observation beam paths within a stereo microscope consists of a first and a second optical component that are displaceable in a defined manner along a common optical axis, following which a third, stationary, optical component is arranged. Variation of magnification is achieved by means of defined displacement of the first two optical components. A focusing on a desired object plane can be effected by displacement of only the first optical component. The pancratic magnification system is arranged after a common main objective for said at least two observation beam paths within the stereo microscope.

11 Claims, 3 Drawing Sheets

PANCRATIC MAGNIFICATION SYSTEM

BACKGROUND OF THE INVENTION

1. Field of the Invention

The present invention relates to a pancratic magnification system for at least two observation beam paths. The pancratic magnification system according to the invention is particularly suitable in a stereo microscope designed as a surgical microscope.

Known stereo microscopes which are constructed on the telescope principle usually include a main objective which is common to the two stereoscopic observation beam paths. The main objective can in this case be designed either with a fixed focal length or else with a variable focal intercept. As a rule, a pancratic magnification system is arranged after the main objective; a separate pancratic magnification system is normally provided for each of the two stereoscopic observation beam paths. Such separate pancratic magnification systems for the individual observation beam paths, however, increase the cost in many ways. Thus the pancratic magnification systems have to be adjusted precisely with respect to each other as regards image position and parallelism of the optical axes. Moreover an expensive mechanism, which does not impair the state of precise adjustment of the optical elements when the magnification is varied, is required for the two pancratic magnification systems. Moreover, a higher production cost also arises with respect to the optical elements, since these are needed in a doubled quantity.

The cost described above is furthermore at least doubled when an additional pancreatic magnification system is to be made available, perhaps for a co-observer.

2. Discussion of Prior Art

To solve these problems, it is known from the German Laid-Open Patent Applications DE 41 23 279, DE 43 36 715 and DE 42 12 924 to arrange behind the main objective a pancratic magnification system having a free diameter dimensioned large enough for both observation beam paths to pass in common through the pancratic magnification system. The increased cost mentioned above is thereby basically reduced.

However, in this known design of the pancratic system, it is disadvantageous that its construction is relatively voluminous for the selected magnification range and can no longer be fitted into a housing which is compact for ergonomic reasons. An expensive folding of the beam path by means of a series of mirrors or prisms is therefore necessary, which again increases the required cost and makes a simple control of the moving components of the pancratic system very difficult.

SUMMARY OF THE PRESENT INVENTION

The present invention therefore has as its object to provide, for at least two observation beam paths in a stereo microscope according to the telescope principle, a common pancratic magnification system which uses as few optical elements as possible, is of compact construction, and in which a simple control of the required movable components is ensured.

According to the invention, a pancratic magnification system is provided which is common to at least two observation beam paths, and which consists of a total of only three optical components. Starting from the object plane in the direction of beam propagation, the first and second optical components behind the main objective are displaceable, to vary the magnification, in a defined manner along a common optical axis. The third optical component, however, is arranged stationary in the observation beam paths.

The pancratic magnification system according to the invention, besides variation of magnification by defined displacement of first and second optical components, also enables focusing on a desired object plane within a given range by displacement of only the first optical component. Thus an inner focusing is also effected within a stereo microscope by means of the pancratic magnification system according to the invention.

Because of the compact construction of the linearly arranged pancratic magnification system with the selected extension factor or magnification range, a simple control of the movable optical components along linear guides is provided. This takes place in a particularly advantageous manner with two separate stepping motors, which are respectively controlled by means of a suitable central control unit. A series of different embodiments exist for the arrangement of the stepping motors.

Alternatively to the stepping motor variants, however, known pancratic mechanisms with cam controls can always be used; they make possible a manual or purely mechanical linear displacement of the individual movable optical components. Such cam controls can be driven either manually or else by means of commercially obtainable motors. Thus manifold possibilities are available for motor drives and corresponding drive designs.

The desired reduction of the production costs results from the halving of the required number of lenses in comparison with the pancratic magnification system with separate stereoscopic beam paths.

Moreover the cost for the precise adjustment of the image positions and of the optical axes of the two stereoscopic partial images does not arise.

The imaging, with exactly the same pancratic magnification, of the two stereoscopic partial images moreover fulfills a further important quality feature for a good stereoscopic image impression.

DESCRIPTION OF THE DRAWINGS

Further advantages, and also details, of the optical device according to the invention will become apparent from the following detailed description of preferred embodiments, with reference to the accompanying drawings, in which:e

DETAILED DESCRIPTION OF PREFERRED EMBODIMENTS

Figure 1:
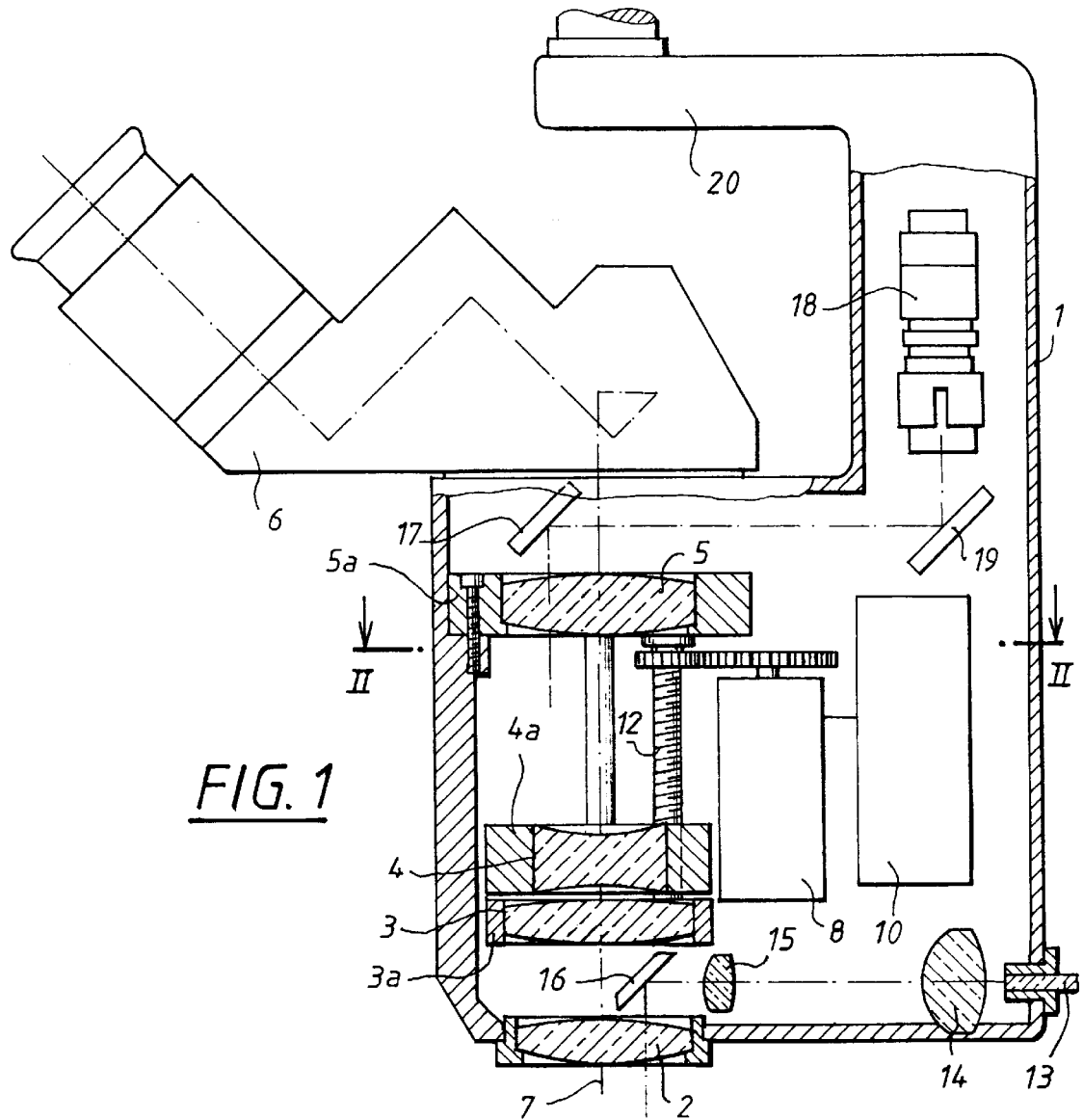
FIG. 1 shows a lateral, partially sectional diagram of a first embodiment of a stereo microscope, which is constructed on the telescope principle, with the pancratic magnification system according to the invention, and which is particularly suitable as a surgical microscope.

FIG. 1 shows a partial sectional representation of a preferred embodiment of a stereo microscope with the pancratic magnification system according to the invention, the microscope being particularly suitable as a surgical microscope.

In this case, a fixed focal length main objective (2) is arranged in the housing (1) of the surgical microscope, and has two stereoscopic observation beam paths passing through it. Starting from the object plane, and arranged after the main objective (2), the pancratic magnification system according to the invention follows in the direction of beam propagation.

Figure 2:
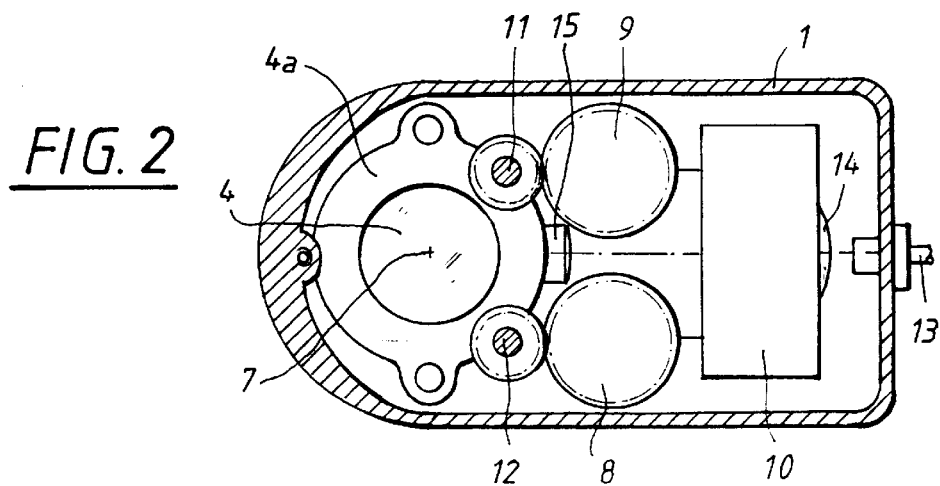
FIG. 2 shows a sectional diagram, in a plan view, of the embodiment of FIG. 1.

Besides a main objective of fixed focal length as described in the embodiment of FIGS. 1 and 2, a main objective with variable focal intercept can be installed in the stereo microscope, as is known from the German Utility Model G 90 03 458.9. Focusing independently of the pancratic magnification system is possible by the use of such a main objective of variable focal intercept, and can if necessary encompass even a greater focusing range than the inner focusing by means of the pancratic magnification system according to the invention, as is further explained hereinbelow. The main objective of variable focal intercept can be embodied as desired, to be adjustable manually or else by motor, via suitable motor drives.

The embodiment shown is FIG. 1 includes three optical components (3, 4, 5). The individual components (3, 4, 5) are mounted in suitable lens mounts (3a, 4a, 5a). The pancratic magnification system, or the individual components (3, 4, 5) of the magnification system, are now dimensioned large enough in free diameter that at least two stereoscopic observation beam paths can pass in common through the pancratic magnification system.

The lens sections of the individual optical components are shown only simplified in FIG. 1; that is, the construction as described hereinbelow of the pancratic magnification system is not directly visible from FIG. 1, but corresponds to the detailed illustration of FIG. 3.

Figure 3:
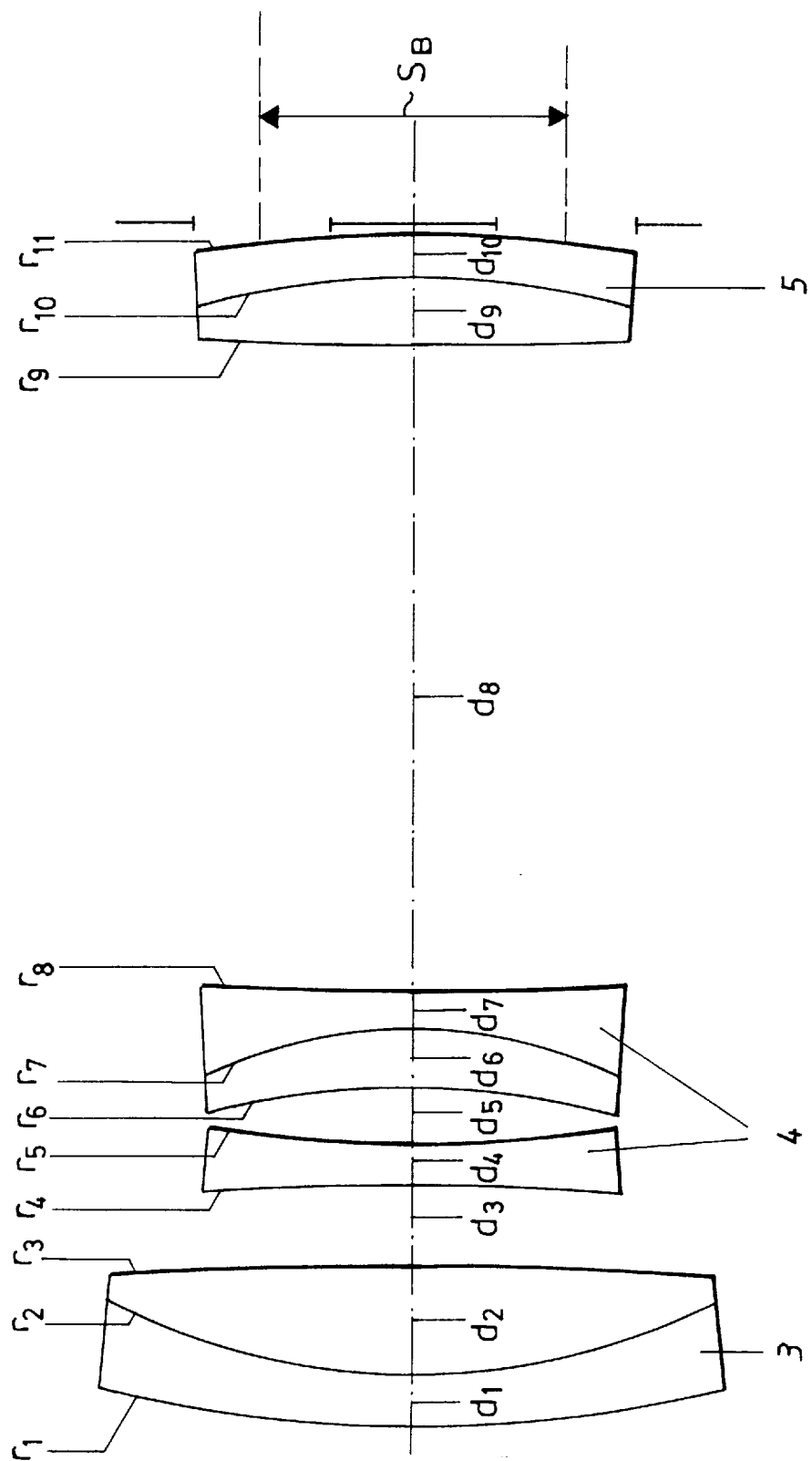
FIG. 3 shows a section through an embodiment of the pancratic magnification system according to the invention, with the corresponding reference symbols for the related lens radii, lens thicknesses, and lens spacings, according to Table 1.

Both the first optical component (3) and also the third optical component (5) are respectively embodied as two-part cemented elements with converging optical action in the embodiment of FIG. 3, yet to be described. The second optical component (4) consists of a cemented element and a single lens, and has a divergent optical action. The first and second optical components (3, 4) are respectively displaceable, in a defined dependence relative to each other, along a common optical axis (7) of the overall optical system of the main objective (2) and the pancratic magnification system. However, the third optical component (5) is arranged stationary in the housing (1) of the surgical microscope, in the stereoscopic beam paths. The desired variation of magnification within a given range is possible by a defined displacement of the first two optical components (3, 4). In the embodiment described hereinbelow, a variation factor of 2 is provided, which is fully adequate for a series of applications, such as for example in ophthalmic and cataract surgery. The magnification Γ of the pancratic magnification system can be varied, in the embodiment described hereinbelow, in the interval Γ=[0.7 . . . 1.4].

The pancratic magnification system according to the invention also permits focusing on a desired object plane, by the displacement of only the first optical component (3) in the beam paths; that is, besides the variation of magnification, a so-called inner focusing is thus also possible. In this case, with a main objective focal length of 200 mm, focusing in a range of ±10 mm can be effected.

In the embodiment shown, the defined positioning of the two displaceable optical elements (3,4) takes place by means of two separate motor drives (8, 9), of which only one is visible in the diagram of FIG. 1. In the diagram of FIG. 2, the adjacently arranged second motor drive (9), which serves for the defined positioning of the second optical element (4) in the beam paths, can be clearly distinguished.

The displacement of the individual optical elements along the optical axis takes place by means of the motor drives (8, 9) either simultaneously or by means of separate or successive displacement movements.

The motor drives (8, 9) are embodied as stepping motors in the embodiment of FIG. 1 and are controlled in a defined manner by means of a central control unit (10). One or more operating elements (not shown) are provided for this purpose on the housing (1) of the surgical microscope; the operator sets the desired magnification setting by means of the operating elements and the setting is then converted by the central control unit (10) into corresponding signals to control the two stepping motors (8, 9) to displace the optical elements (3,4) into the corresponding required lens positions. The displacement of the two movable optical elements (3,4) takes place along guides, which are embodied as threaded spindles (11, 12) in the embodiment example shown, and which are connected on one side with the mounts (3a, 4a) of the two optical elements (3, 4) and on the other side with the respective drive motors (8, 9) by means of a suitable drive transmission mechanism.

The stepping motors (8, 9) provided for the displaceable optical elements (3, 4) moreover have detectors that sense the respective present position of the optical element (3, 4) on the optical axis (7) and continuously transmit corresponding position information to the central control unit (10). For this purpose, known incremental or absolute encoders are suitable, such as those offered, for example, in great variety by the HEIDENHAIN Company.

Analogously to the variation of magnification, motorized inner focusing by the user is possible by defined driving of the stepping motor for the first optical element (3). A corresponding operating element (not shown) is provided on the surgical microscope for this purpose.

Besides the arrangement of the operating elements in the form of suitable switches located directly on the housing (1) of the surgical microscope, it can be required for certain applications to provide an operating unit in the form of a hand or foot control console, separate from the surgical microscope. Such a separate operating unit does not, however, change the principle of activation of the motorized functions.

It has moreover been found to be advantageous to provide, both for the motorized variation of magnification and for motorized focusing, a so-called "homing function"; that is, to offer the user the possibility, once magnification and/or focusing settings have been set, of automatically reverting to these settings after a displacement. For this purpose, these desired positions or settings are sensed by the control unit (10), by means of the detectors provided, and are stored in a so-called "look-up table". If the identical setting is later desired again, the corresponding position information is read out by the control unit (10) from the look-up table, and corresponding control signals to travel Lo these positions are transmitted to the motor drives (8, 9), which are embodied as stepping motors.

Alternatively to the purely motorized displacement of the respective optical elements as described hereinabove, in a less expensive embodiment a known mechanical cam control for the displaceable optical elements of the pancratic magnification system according to the invention can be provided, and is manually actuated.

An illuminating unit is moreover arranged in the housing (1) of the operation microscope shown, between the main objective (2) and the optical elements (3, 4, 5). Here the illuminating unit includes a preferably fiber optic light guide (13), into which the radiation of a desired source is coupled on the input side with high efficiency. The radiation leaving the fiber optic light guide (13) is conducted towards a deflecting element (16) by means of two optical beam dimensioning elements (14, 15) in the form of suitable lens systems. The deflecting element (16) deflects the illuminating light in the direction of the object plane at a defined angle.

Besides the schematically shown arrangement of the individual elements of the illuminating unit, various further possibilities of arrangement are of course possible, for example, for the deflecting elements and the like in connection with the pancratic magnification system.

In the embodiment shown, after the pancratic magnification system there follows, in the direction of the observer, a known stereoscopic binocular tube (6) as the observation unit by means of which the observer obtains a direct visual impression of the observed object. The binocular tube (6) has here an optical construction which is known in principle, as set forth, for example, in U.S. Pat. No. 4,175,826, which issued Nov. 27, 1979.

Moreover, a deflecting or beam-splitting element (17) is arranged in the observation beam paths between the binocular tube (6) and the pancratic magnification system. The coupling-out of a given fraction of the observation beam paths, in the direction of a documentation unit (18) with at least one electronic image recorder, takes place by means of this beam splitter element (17). In the embodiment shown, the deflection of the coupled-out beam path fraction by means of a further deflecting element (19) towards the documentation unit (18) is necessary for this purpose. The documentation unit (18) is integrated directly into the housing (1) of the surgical microscope and is embodied as a known 1-chip camera. The signal generated by means of this electro-optical detector arrangement (18) can then be further processed in a known documentation-like manner, that is, for example, stored and/or reproduced on a display.

Alternatively, the electro-optical detector arrangement can be arranged in a known manner outside the housing proper.

Moreover, in a further embodiment, the deflecting element (19) can be designed to be pivotable into the beam path. According to the position in which the deflecting element (19) is located, the electro-optical detector arrangement (18) will then be acted on as shown in FIG. 1 or else this beam path will be fed to a known co-observer microscope.

If a documentation by means of the electro-optical detector arrangement (18) and also observability by a co-observer are simultaneously desired, the deflecting element (19) can preferably be designed to be partially transmissive or partially reflecting. That is, the transmission or reflection properties of the deflecting element are to be adjusted, for example to a transmission ratio of 50:50, etc., according to the desired intensity ratio in the co-observer beam path and in the documentation beam path.

It is furthermore also possible to provide, instead of the binocular tube as an observation unit, only a documentation unit with at least one electro-optical detector arrangement; that is to design the stereo microscope with the pancratic magnification system according to the invention as a purely video stereo microscope.

Furthermore the operation microscope shown in FIG. 1 has a connecting element (20) by means of which it can be arranged on a known support system.

A plan view of a portion of the embodiment example of FIG. 1 is shown in FIG. 2. The identical elements are denoted in both Figures with the same numerals. The two motor drives (8, 9), embodied as stepping motors, and also their drive spindles (11, 12), by means of which the movable optical components are displaced along the optical axis (7), are now clearly distinguishable. As previously described, the central control unit (10), which controls the defined operation of the respective optical components (3, 4) as prescribed by the observer, is connected to the two drives (8, 9).

The pancratic magnification system according to the invention has also been found to be advantageous when more than only two observation beam paths are required. Thus, for example, as already indicated in FIG. 1, a documentation beam path, or a single observation beam path for monocular co-observation, can be coupled out, and has identically the same magnification as the two observation beam paths of a main observer. She same analogously holds for the case of a stereoscopic co-observer microscope, so that a symmetrical division of the total of four observation pupils is then present over the cross section of the pancratic magnification system through which the beams pass in common.

Because of the now relatively large free diameter of the pancratic magnification system, one or more such beam splitter elements (17) can be arranged relative to the observation pupils of the main observer, without resulting in a troublesome limitation of the observation pupils.

The lens section of the embodiment of the pancratic magnification system according to the invention is shown in FIG. 3. The position of the optical components on the optical axis (7) in relation to each other corresponds here to a magnification $\Gamma=0.7$.

The reference symbols for the individual optical components (3, 4, 5), and also the lens radii $r_i$, lens thickness $d_i$, and lens distances $d_i$, as specified in the following set of data of Table 1, are given in FIG. 3.

The embodiment shown of the pancratic magnification system includes—listed from left to right—a first convergent optical component (3), which is embodied as a two-part cemented member. This is followed by a second, divergent, optical component (4), consisting of a two-part cemented member and a single lens at a defined distance therefrom, both the cemented member and the single lens respectively having a divergent action. The third optical component (5) of the pancratic magnification system according to the invention has a convergent optical action and is embodied as a two-part cemented member. Here the third optical component (5) is arranged to be stationary in the stereoscopic beam paths, while the first and second optical components (3, 4) are arranged to be displaceable along the common optical axis (7). A variation of the magnification within a given interval is possible, as already mentioned, by means of the defined displacement of these two optical elements (3, 4). The magnification which can be attained lies in the range of $\Gamma=[0.7\ldots1.4]$ in the embodiment set out in the following Table 1. This corresponds to a zoom factor or scale factor of 2 for the pancratic magnification system. This is completely adequate for a series of applications.

As has already been stated, focusing on a desired object plane is possible by a displacement of the first optical component (3) along the optical axis (7). The variation $\delta S$ of focal intercept which is thereby possible amounts to about δS=±10 mm for a main objective focal length of 200 mm and a displacement range of the first optical component (3) of about ±5 mm.

The pancratic magnification system according to the invention is now so compactly constructed as regards its size that it can be arranged in a housing which is no larger than that for a conventional surgical microscope, and thus fulfills the corresponding ergonomic requirements.

The specific optical data of an embodiment of the pancratic magnification system according to the invention are set out in the following Table 1. The respective radii of curvature of the individual lenses are denoted by $r_i$, and the distances between the optically effective surfaces of the pancratic magnification system along the optical axis are denoted by $d_i$. Distances $d_3$ and $d_8$ are the intervals given in Table 1 for the distances to the respectively adjacent optically effective surfaces, which correspond, as previously explained, to a magnification interval.

Variation of the distance $d_3$ of about ±5 mm serves, moreover, for the variation of the focal intercept, as mentioned; that is, for the desired inner focusing.

Moreover the respective reference symbols for the medium, kinds of glass used for the individual elements of the embodiment shown, are set out in the following Table 1. The different kinds of glass may be ordered from the Firm of Schott Glaswerke, Mainz, under these reference symbols.

Furthermore, the free diameter $D_F$ the individual optical elements is also given. The maximum free diameter $D_F$ within the embodiment shown here amounts to about 45 mm, which corresponds to the requirement for compactness and to the smallest possible optical correction requirements.

In the illustration of FIG. 3, the position of the two stereo pupils is shown. They lie in a plane which lies between the third optical component (5) and the binocular tube provided or, furthermore, a documentation device.

The resulting stereo base $S_B$, that is, the distance of the optical axes of the two stereoscopic observation beam paths, is likewise shown. In this case, it amounts to 22 mm.

TABLE 1

| Radius $r_i$, mm | Thickness or distance $d_i$, mm | Free diameter $d_F$, mm | Medium |
|---|---|---|---|
| $r_1$ = 92.6627 | $d_1$ = 4.000 | 45.300 | SD56A |
| $r_2$ = 48.8915 | $d_2$ = 8.000 | 44.000 | SSKN8 |
| $r_3$ = −299.1397 | $d_3\epsilon$ \| 5.904; 41.021\| | 43.700 | air |
| $r_4$ = −184.6478 | $d_4$ = 3.000 | 30.400 | BAK2 |
| $r_5$ = 93.9299 | $d_5$ = 4.000 | 29.700 | air |
| $r_6$ = −57.5094 | $d_6$ = 4.000 | 29.700 | SF57 |
| $r_7$ = −35.1813 | $d_7$ = 3.000 | 30.200 | SK5 |
| $r_8$ = 328.0925 | $d_8\epsilon$ \| 46.596; 2.979\| | 30.900 | air |
| $r_9$ = 429.4695 | $d_9$ = 5.000 | 31.300 | SSKN8 |
| $r_{10}$ = −52.4473 | $d_{10}$ = 3.000 | 31.500 | SF56A |
| $r_{11}$ = −96.7737 | | 32.000 | |

The embodiment in FIG. 3 or Table 1 of course represents only one possible embodiment of the pancratic magnification system according to the invention; that is, an alternative design is also possible by means of corresponding variations of the optical data.

Further preferred embodiments for a stereo microscope with the pancratic magnification system according to the invention are described hereinbelow with reference to FIGS. 4 and 5.

Figure 4:
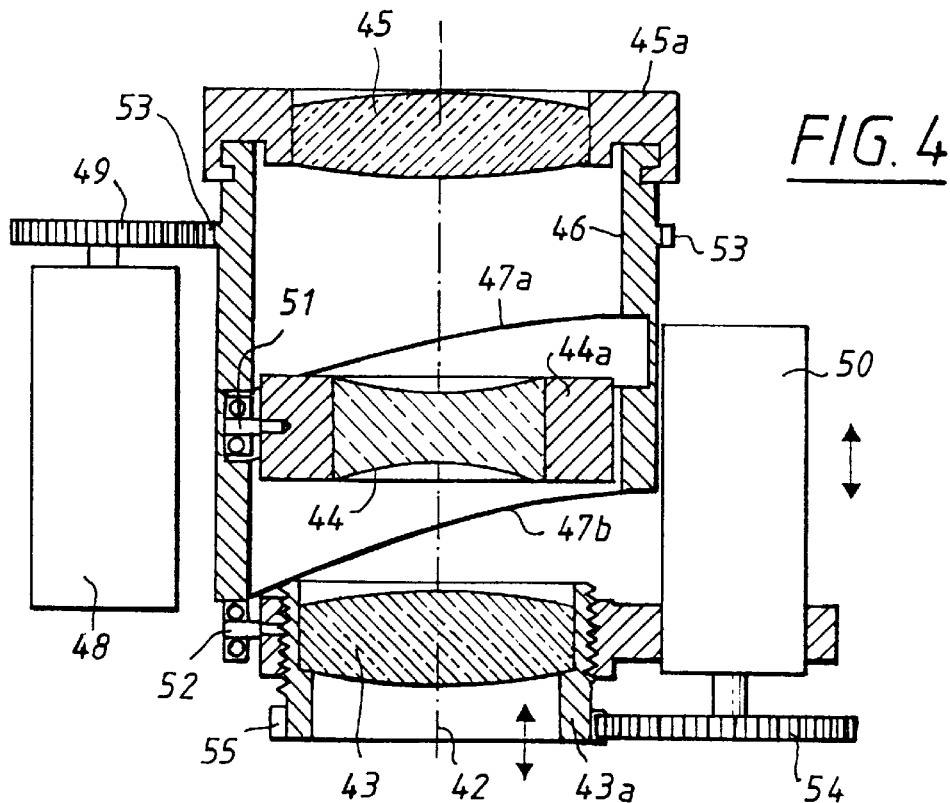
FIG. 4 shows a further preferred embodiment of a stereomicroscope with a motor controlled pancratic system according to the invention.
Figure 5:
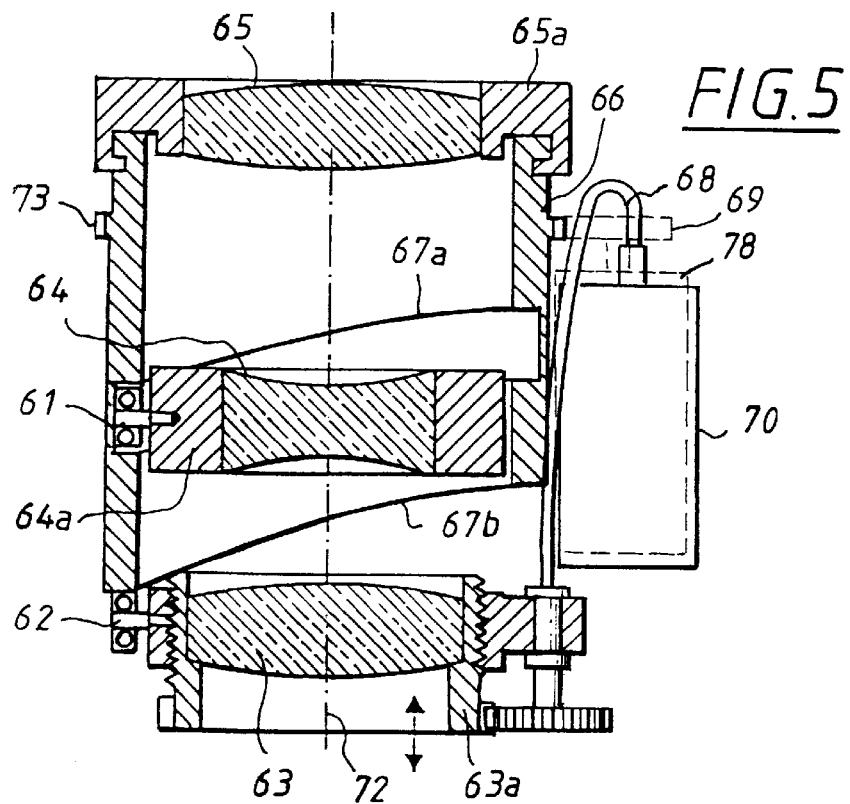
FIG. 5 shows another preferred embodiment of a stereomicroscope with a motor controlled pancratic system according to the invention.

In both FIGS. 4 and 5, only a portion of a stereo microscope designed as a surgical microscope in which the pancratic magnification system according to the invention is arranged, is shown.

Alternatively to the embodiment shown in FIGS. 1 and 2, in the two embodiments shown in FIGS. 4 and 5, the defined movement of the optical components of the pancratic magnification system is effected by means of other arrangements of the motor drives. In particular, stepping motors are now no longer used; instead, conventional motors drive corresponding cam controls.

In the embodiment of FIG. 4, the two moveable optical components (43, 44) are arranged in corresponding lens mounts (43a, 44a) which can be displaced along optical axis (42). The two movable optical components (43, 44) or the lens mounts (43a, 44a) are moved in a cylindrical sleeve (46) that is equipped with two control cams (47a, 47b) engaged by guide elements (51, 52) connected to the lens mounts (43a, 44a).

If a change of the magnification is now to take place, the cylindrical sleeve (46) is displaced by the adjacently arranged motor (48) in a rotary motion. For this purpose, the gearwheel (49) provided on the motor engages in a toothed ring (53) that is arranged with radial symmetry around the sleeve (46). The two movable optical components (43, 44) are then moved corresponding to the chosen control cam pitch along the optical axis (42). The focusing of the pancratic magnification system according to the invention takes place in this embodiment by means of a second motor (50), which displaces solely the first optical component (43) along the optical axis (42). The second motor (50), for this purpose, transfers a rotary motion, likewise by means of a gearwheel (54) which engages in a toothed ring (54) on the lens mount (43a) of the first optical component (43), into the required linear motion along the optical axis (42). The second motor (50) is thus displaced, together with the first optical component (43), during a variation of magnification, by means of the rotary motion of the sleeve.

A further embodiment of a drive design for the pancratic magnification system according to the invention is shown in FIG. 5.

The drive of the two movable optical components (63, 64) again takes place by means of two separate motors (78, 70) which are arranged adjacently as in the embodiment of FIGS. 1 and 2. Motor (78) engages via a gearwheel (69) in the toothed ring (73), which is arranged around the cylindrical housing (66) that guides the two movable optical components (63, 64) along the control cams (67a, 67b). The third optical component (65) is again arranged fixedly in the stereoscopic beam paths.

In order to avoid having an associated motion of the motor drive for the focusing when the magnification is changed, as is the case in the embodiment of FIG. 4, the drive motion of the fixedly arranged second motor (70) for the optical component (63) is transmitted by means of a flexible shaft (68). The positioning of the first optical component (63) along the optical axis (72) takes place by means of the driven flexible shaft (68), to thus effect the desired inner focusing of the pancratic magnification system according to the invention.

We claim:

1. A pancratic magnification system for at least two observation beam paths, comprising:
   a first optical component and a second optical component that are displaceable along a common optical axis in a defined manner, and
   a third optical component that is stationary following said first and second optical components,
   wherein a variation of magnification; is effected by means of a defined displacement of said first and second optical components, wherein focusing on a desired object plane is effected by displacement of only said first optical component, and wherein said first, second, and third optical components comprise a plurality of individual lenses having the following optical data:

| Radius $r_i$, mm | Thickness or distance $d_i$, mm | Free diameter $d_F$, mm | Medium |
|---|---|---|---|
| $r_1 = 92.6627$ | | 45.300 | |
| | $d_1 = 4.000$ | | SF56A |
| $r_2 = 48.8915$ | | 44.000 | |
| | $d_2 = 8.000$ | | SSKN8 |
| $r_3 = -299.1397$ | | 43.700 | |
| | $d_3 \in \lvert 5.094; 41.021 \rvert$ | | air |
| $r_4 = -184.6478$ | | 30.400 | |
| | $d_4 = 3.000$ | | BAK2 |
| $r_5 = 93.9299$ | | 29.700 | |
| | $d_5 = 4.000$ | | air |
| $r_6 = -57.5094$ | | 29.700 | |
| | $d_6 = 4.000$ | | SF57 |
| $r_7 = -35.1813$ | | 30.200 | |
| | $d_7 = 3.000$ | | SK5 |
| $r_8 = 328.0925$ | | 30.900 | |
| | $d_8 \in \lvert 46.596; 2.979 \rvert$ | | air |
| $r_9 = 429.4695$ | | 31.300 | |
| | $d_9 = 5.000$ | | SSKN8 |
| $r_{10} = -52.4473$ | | 31.500 | |
| | $d_{10} = 3.000$ | | SF56A |
| $r_{11} = -96.7737$ | | 32.000 | | where respective radii of curvature of said individual lenses are denoted by $r_i$, their respective free diameters $d_F$ are set out; distances between optically effective surfaces of said pancratic magnification system are given by $d_i$, and said first and second optical components are displaceable within given limits such that respective distances $d_3$ and $d_8$ are variable within given intervals.

2. Pancratic magnification system according to claim 1 in combination with a main objective arranged before said pancratic magnification system, a housing in which said pancratic magnification system and said main objective are arranged, and in illuminating unit having a fiber optic light guide and at least one deflecting element for deflecting illuminating light ill a direction of an object plane.

3. Pancratic magnification system according to claim 2 in combination with at least one observation unit arranged after said pancratic magnification system for direct visual observation of an object field.

4. Pancratic magnification system according to claim 3 in combination with at least one documentation unit with at least one electro-optical image recorder arranged after said pancratic magnification system.

5. Pancratic magnification system according to claim 4, wherein said documentation unit is arranged in said housing.

6. A pancratic magnification system according to claim 1, further comprising at least one motor drive for displacing said first and second optical components in a defined manner.

7. Pancratic magnification system according to claim 6, wherein said at least one motor drive comprises a stepping motor for each of said first and second optical components, further comprising a central control unit for controlling said stepping motors.

8. Pancratic magnification system according to claim 7, further comprising detectors associated with said stepping motors that sense positions of said first and second optical components on said optical axis, and continuously transmit information concerning said positions to said central control unit.

9. Pancratic magnification system according to claim 6, further comprising a cam control by means of which said first and second optical components can be positioned in defined dependence on each other for setting magnification, wherein said at least one motor drive comprises a first motor that drives said cam control and a second motor connected to said cam control for focusing by means of said first optical component.

10. Pancratic magnification system according to claim 6, further comprising a flexible shaft between said at least one motor drive and said first optical component for transmission of drive motion for said first optical component for focusing.

11. A pancratic magnification system according to claim 1 used in a surgical microscope.

* * * * *